United States Patent [19]
Errico et al.

[11] Patent Number: 5,810,818
[45] Date of Patent: Sep. 22, 1998

[54] SPINAL HOOK IMPLANT HAVING A LOW BLADE AND S SWIVEL HOOK

[75] Inventors: Joseph P. Errico, Far Hills; Thomas J. Errico, Summit, both of N.J.; Julius R. Falcon, Greensburg, Pa.; James D. Ralph, Oakland; Stephen Tatar, Montville, both of N.J.

[73] Assignee: Fastenetix, LLC, Summit, N.J.

[21] Appl. No.: 880,809

[22] Filed: Jun. 23, 1997

Related U.S. Application Data

[63] Continuation-in-part of Ser. No. 547,106, Oct. 23, 1995, Pat. No. 5,688,274, and Ser. No. 659,083, Jun. 3, 1996, abandoned.

[51] Int. Cl.$^6$ ............................................. A61B 17/70
[52] U.S. Cl. ................................................. 606/61; 606/72
[58] Field of Search ............................. 606/61, 60, 72, 606/73; 623/17

[56] References Cited

U.S. PATENT DOCUMENTS

| | | |
|---|---|---|
| 5,263,954 | 11/1993 | Schlapfer et al. ..................... 606/61 |
| 5,476,464 | 12/1995 | Metz-Stravenhagen et al. ........ 606/61 |
| 5,534,001 | 7/1996 | Schlapfer et al. ....................... 606/61 |
| 5,584,832 | 12/1996 | Schlapfer .............................. 606/61 |
| 5,688,273 | 11/1997 | Errico et al. ........................... 606/61 |
| 5,688,274 | 11/1997 | Errico et al. ........................... 606/61 |

*Primary Examiner*—Guy V. Tucker
*Attorney, Agent, or Firm*—Joseph P. Errico, Esq.

[57] ABSTRACT

A hook device for use with support rod implantation apparatus is disclosed which is positionable along the central axis of the posterior surface of the spine and has independently rotationally positionable blade and head portions. The head portion is engageable with a deflecting top cylindrical portion which sits above the lamina. The insertion, and subsequent locking of a rod in the rod receiving channel of the head portion causes the blade portion and the head portions to be compression locked together by virtue of an interference fit.

8 Claims, 9 Drawing Sheets

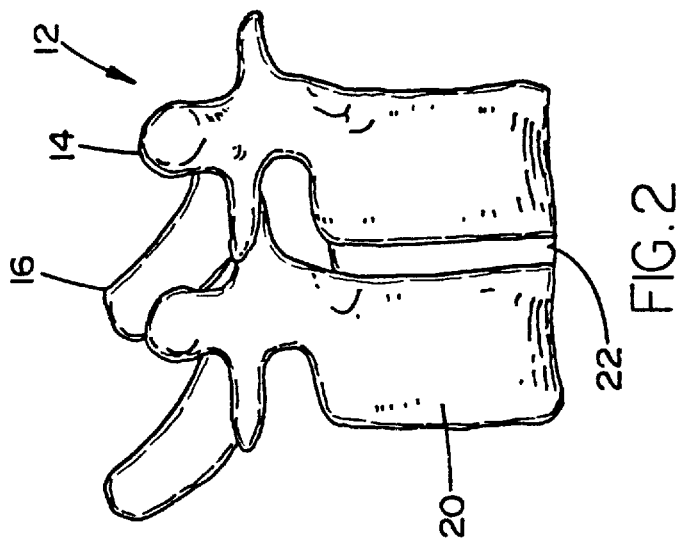
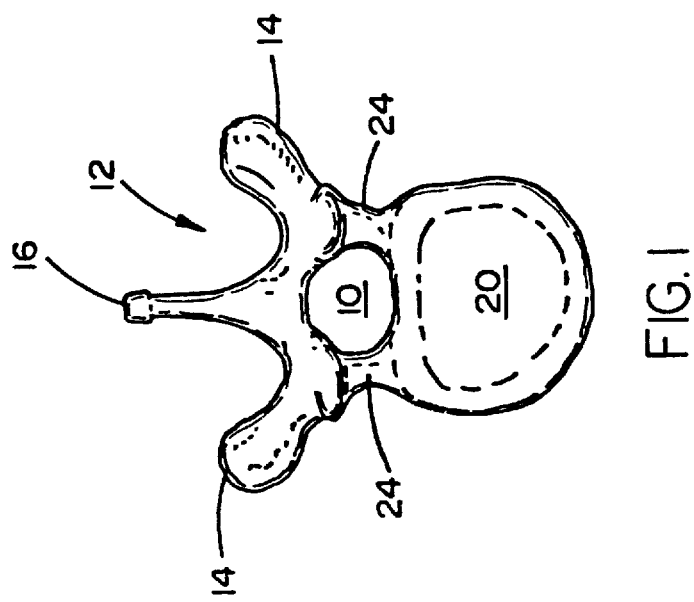

5,810,818

SPINAL HOOK IMPLANT HAVING A LOW BLADE AND S SWIVEL HOOK

BACKGROUND OF THE INVENTION

Cross-Reference to Related Application

This application is a continuation-in-part of applications U.S.S.N.'s 08/547,106,filed Oct. 23, 1995,now U.S. Pat. No. 5,688,274 and 08/659,083, filed Jun. 3, 1996, now abandoned entitled "A Spinal Implant Device Having A Single Central Rod Having Plow And/Or Claw Hooks" and "A Spinal Hook Device Having A Rotating Head", respectively.

FIELD OF THE INVENTION

This invention relates generally to a hook and rod implant apparatus for immobilization of the spinal column. More particularly, the present invention relates to an implant apparatus comprising hook devices for attaching to the posterior lamina at a central position thereon, having a rotateable head for receiving a single support rod.

Discussion of the Prior Art

The bones and connective tissue of an adult human spinal column consist of an upper portion having more than 20 discrete bones, and a lower portion which consists of the sacral bone and the coccygeal bodies. The bones of the upper portion are generally similar in shape, as will be more fully described hereinbelow with respect to FIGS. 1, 2 and 3. Despite their similar shape, however, they do vary substantially in size in accordance with their individual position along the column and are, therefore, anatomically categorized as being members of one of three classifications: cervical, thoracic, or lumbar. The cervical portion, which comprises the top of the spine, up to the base of the skull, includes the first 7 vertebrae. The intermediate 12 bones are the thoracic vertebrae, and connect to the 5 lumbar vertebrae.

The lower portion of the spinal column, which extends into the hip region is primarily comprised of the sacral bone. This bone is unlike the other bones of the spinal column, in both shape and size. In fact, at birth humans have five distinct sacral bones which begin to fuse together during childhood, and by adulthood have fully combined. For the purpose of describing this invention, however, the sacral bone shall be referred to as distinct from the spinal column; the spinal column, therefore, comprising for the purposes of this description, only the cervical, thoracic, and lumbar vertebrae.

The bones of the upper portion vary in size, but are each similarly coupled to the next by a tri-joint complex. The tri-joint complex consists of an anterior disc and the two posterior facet joints, the anterior discs of adjacent bones being cushioned by cartilage spacers referred to as intervertebral discs. Referring now to FIGS. 1, 2 and 3, top, lateral, and posterior views of a typical vertebral bones of the spinal column are shown. The spinal cord is housed in the central canal 10, protected from the posterior side by a shell of bone called the lamina 12. The lamina 12 has three large protrusions, two of these extend laterally from the side ends thereof and are referred to as the transverse processes 14. The third extends back and down from the center of the lamina and is called the spinous process 16. The lamina 12 defines an arched shape about the posterior of the spinal cord, the arched shape having lateral portions 13a,13b which are generally straight, and which meet beneath the spinous process at a curved surface 15.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

Referring specifically to FIG. 3, the stacking of vertebrae is shown from the posterior. From the posterior, each vertebra is coupled to the one above and below via facet joints 19 on either side of an opening into the spinal canal 10.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column.

These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally by coupling to the pedicles via screws, or by means of hooks which attach under the lamina, and entering into the central canal. In either case, the implants generally comprise at least one (and usually a pair thereof) elongate support rod element which is coupled to the screws or hooks to immobilize several sequential vertebrae, for example to hold them stable so that the adjacent bones may be fused with bone graft. The prior co-pending application, U.S.S.N. 08/502,285, of which this application is a continuation-in-part, discloses novel devices which provide significantly superior performance for such implants which comprise screws for coupling to the pedicles. Inasmuch as the pedicles are disposed laterally with respect to the posterior profile of the column of vertebrae, the rods of such screw systems have universally been disposed to the sides of the central axis of the spine, lateral to the axis formed by the spinous processes. As set forth more fully hereinbelow, the disposition of the rods in the natural site for desired bone fusion, limited bone graft can be achieved. Maximal posterior bone fusion is desired for all immobilizations of such portions of the spine, and therefore, the placement of the rod in the best site for such bone growth is a drawback of lateral systems.

Hook and rod assemblies however, have not provided any superior access to the lateral portions of the posterior surfaces of the spine. Generally hook and rod assemblies of the prior art have included a plurality of hooks having linear blade portions which are inserted posteriorly under the straight portion of the lamina between the transverse process and the spinous process (off the center line of the spine). The hooks include upper body portions to which the support rod is coupled.

Referring now to FIGS. 4 and 5, U.S. Pat. No. 5,005,562 to Cotrel teaches such a hook and rod apparatus which includes a pair of rods 30a,30b, which are coupled to hooks 32a,32b and 34a,34b. Upper hooks 32a,32b are disposed such that the blade portions are directed downward, hooking the straight (side) portion 13a,13b of the lamina 12 which is sequentially below them. Lower hooks 34a,34b are disposed in the opposite orientation, so that the blade portions thereof are directed upward relative to the axis of the spine. It is understood that the rods 30a,30b are also coupled to pedicle screws 36a–36d. The rods 30a,30b hold the hooks 32a–b, 34a–b to the lamina 12, preventing their movement out from beneath their respective lamina 12 by virtue of tensile rigidity in the rod. In addition, the rods 30a,30b are further stabilized by cross link devices 38a,38b. It is clear from FIG. 4 that there is little free space to place bone graft material, and in fact where such bone graft may ultimately grow is precisely where the implant is positioned, thereby risking difficulty of removal if long term post-operative problems necessitate removal of repair of the apparatus.

FIG. 5 illustrates one specific type of hook, the ones disclosed by U.S. Pat. No. 5,005,562. These hooks have a blade portion, including a flat extending member 51 which is designed to fit snugly to the undersides of the flat portions 13a,13b of the lamina 12 which is next to the transverse processes (on either side of the spinous process). This hook further includes an integrally formed rod receiving body 52, which extends upwardly from the top of the blade portion 55. The rod receiving body 52 comprises a generally cylindrically shaped portion 54 having a vertical slot 58 formed in the top thereof for receiving the rod 30a or 30b. This rod is secured in the slot 58 by a threaded plug 56.

In addition to the disadvantages of the laterally disposed rod apparatuses, with respect to the availability of free space in which to introduce bone graft material, it has been identified that hooks having flat extending members which are disposed under the flat portion of the lamina 13a,13b may cause undue stress concentrations in the laminar bone. This is in part due to the location of the blade, the narrowness of the blade, as well as the torquing which the lateral offset implies. In addition, it is a function of the relative thinness of the lamina 12 at these sites.

Further, it has been found that considerable difficulty may be associated with inserting hooks under sequential lamina along a misaligned curvature while simultaneously exactly positioning their rod receiving portions thereof such that they are aligned so that the rod can be passed therethrough without distorting, tilting, rotating, or exerting undesired translational forces on the hooks. Correction of this difficulty requires the time consuming and difficult task of reshaping the rods or repositioning the hooks, each of which is understood to require considerably longer operating time, which is known to increase the incidence of complications associated with surgery. Often such alignments with such fixed body hooks cannot be satisfactorily achieved, and the entire instrumentationing effort has to be altered to utilizing screws. Any such time consuming efforts which afflict the implantation of a single rod assembly is understandably amplified with the necessity of implanting a parallel apparatus on the opposing lateral extent of the posterior of the spinal column.

It is, therefore, the principal object of the present invention to provide a single center axis hook and rod implant system to maximize desirable area for bone grafting purposes.

It is also a principal object of the present invention to eliminate the need for a second parallel apparatus to be implanted to stabilize and immobilize sequential vertebrae.

It is, relatedly, an object of the present invention to provide a simplified implantation apparatus which reduces the amount of operative time necessary for proper introduction thereof.

It is still further an object of the present invention to provide an implant apparatus which reduces the point stress loads on the laminar bones of the spine.

It is another principal object of the present invention to provide a lamina hook which may be utilized in accordance with the above objects.

It is relatedly an object of the present invention to provide a lamina hook having a rod coupling body which provides a polyaxial freedom of implantation angulation with respect to rod reception.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a single axis, centerline, lamina hook and rod apparatus. The hook elements of this invention include swiveling heads which permit easy alignment of the head of the hook with the central axis rod. The hooks are designed to be seated beneath the thickest and widest portion of the lamina, i.e., beneath the central arch of the lamina, ensuring significant strength enhancement, and correspondingly reduced concern for laminar bone breakage at the hook-bone interface. These blades further provide self alignment to the hook relative to rotational forces which may be applied thereto.

In the principal embodiment, the blade portion comprises a curved and arched contoured surface, having a central axis ridge extending parallel to the general rod receiving axis, which seats into the arched undersurface of the central axis of the lamina. The curve is approximated to the arch 15 at the center of the lamina as shown in FIG. 1.

The implantation of such a device may require the removal of the spinous process, inasmuch as a preferred position of the rod receiving body portion of the hook is directly along the centerline of the spine (often defined by the sequence of spinous processes). It is, however, herein noted that the height of the overall construct of the present invention should be less than the anatomical height of the spinous process, therein eliminating a considerable potential for post-surgical pain, which is often associated with laterally placed implant structures (which rise above the bone at places where the presence of the metal prosthesis causes irritation of the surrounding tissues). The spinous process is not a structurally significant feature providing direct support to the spinal column. In fact, the spinous processes is often removed for use as bone graft material, or to provide increased potential bone graft sites in instances wherein there is such a reduction in alternative bone graft site due to the apparatuses implanted (which is an additional advantage of use of the present invention).

The upper portion of the hook includes a plurality of upwardly extending members which mutually define a cylinder having vertically oriented slots separating each individual member. This conformation permits the mutually defined cylindrical shape to deflect inward and outward upon the application a corresponding force. Each of the upwardly extending members comprises a generally uniform radial thickness from its union with the curvate section up to a circumferential position near to the uppermost extent thereof. The uppermost extent thereof, however, comprises a discontinuously widened circumference which subsequently tapers radially inwardly from that vertical position to the upper end. This discontinuously widened circumference thereby defines an annular ledge around the cylindrical top section which ledge tapers inwardly to provide a beveled conformation.

The rod receiving head portion comprises a cylindrical shape having an upper section and a lower section, and an axial bore. The upper section has a vertical channel for receiving a rod therein, defined between upwardly extending members which comprise a threading on the inner and/or outer surface. This threading permits the engagement of a locking nut which may be translated downwardly to provide a corresponding downward force onto the rod. The lower section of the head includes a receiving conformation (part of the axial bore) for retaining and providing an interference locking means for securely holding the blade and head portions together upon the locking of the rod in the channel.

More specifically, the bore of the head portion comprises an inner annular lip which engages the outer annular ledge of the cylindrical top section of the blade portion. Upon coupling, the tapered uppermost ends of the cylindrical top section of the blade deflect inwardly until the annular ledge advances beyond the inner annular lip and they snap back to their undeflected position. The head and blade portions are thereby prevented from separating based on the interference fit of the ledge and lip.

The diameter of the annular lip of the bore is substantially equivalent to the undeflected diameter of the cylindrical top section such that once the blade and head portions are coupled, the two portions may rotate relative to one another. The relative position of the annular lip within the axial bore is set such that the uppermost ends of the cylindrical top section of the blade portion extend above beyond the deepest point of the curvate bottom of the channel. This requires that the rod, once inserted into the channel, rest on top of the cylindrical section of the blade portion (and not on the curvate bottom of the channel).

Subsequent locking down of the rod in the channel, by a locking nut (which engages the top of the channel) causes the head to be drawn upwardly relative to the blade, until the interference of the annular lip of the head and the annular ledge of the top cylinder of the blade portion engage. The friction of this interference serves to lock the head portion at the rotational position, thereby preventing continued swiveling.

In preferred embodiments, the top surfaces of the upwardly extending members of the blade portion, which mutually define the cylindrical section, and which are rotationally freely retained in the interior axial bore of the head portion, include ridges and/or curvate notches which are diametrically paired across the cylindrical section. These notches are so formed such that when the rod is seated thereon and provides a downward force, a resultant radial force, which is directed outward, is generated (thereby causing those upwardly extending member which are in contact with the rod to deflect outward and to supplementarily radially compression lock the blade and head portions). It shall be understood that these notches are positioned between adjacent pairs of the upwardly extending members such that the vertical slots separating each are widened by downward force of the rod thereon.

During implantation of this device, the flat extending section of the blade portion is first positioned under the corresponding lamina. The head portion of the hook is then rotated relative to the blade, such that the rod may easily be inserted into the channel formed therein. The rod is positioned in the channel such that it rests on the top of the cylindrical top section of the blade portion which is coupled in the axial bore of the head portion. The locking nut causes the rod to push down on the cylinder, and to secure the head from rotating relative to the blade via the friction lock of the interfering lip and ledge of the head and blade, respectively.

In the preferred embodiment the rod is further seated in the curvate notches of the uppermost surface of the cylinder. Subsequent engagement of the locking nut on the top threading of the head portion further causes the rod to push down on the cylinder, causing its constituent individual upwardly extending members to deflect outward and lock to the head and blade even more securely.

BRIEF DESCRIPTION OF THE DRAWINGS

FIG. 1 is a top view of a vertebral bone characteristic of those of the cervical, thoracic, and lumbar spine;

FIG. 2 is a side view of sequentially aligned vertebral bones, such as are found in the cervical, thoracic, or lumbar spine;

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 3:
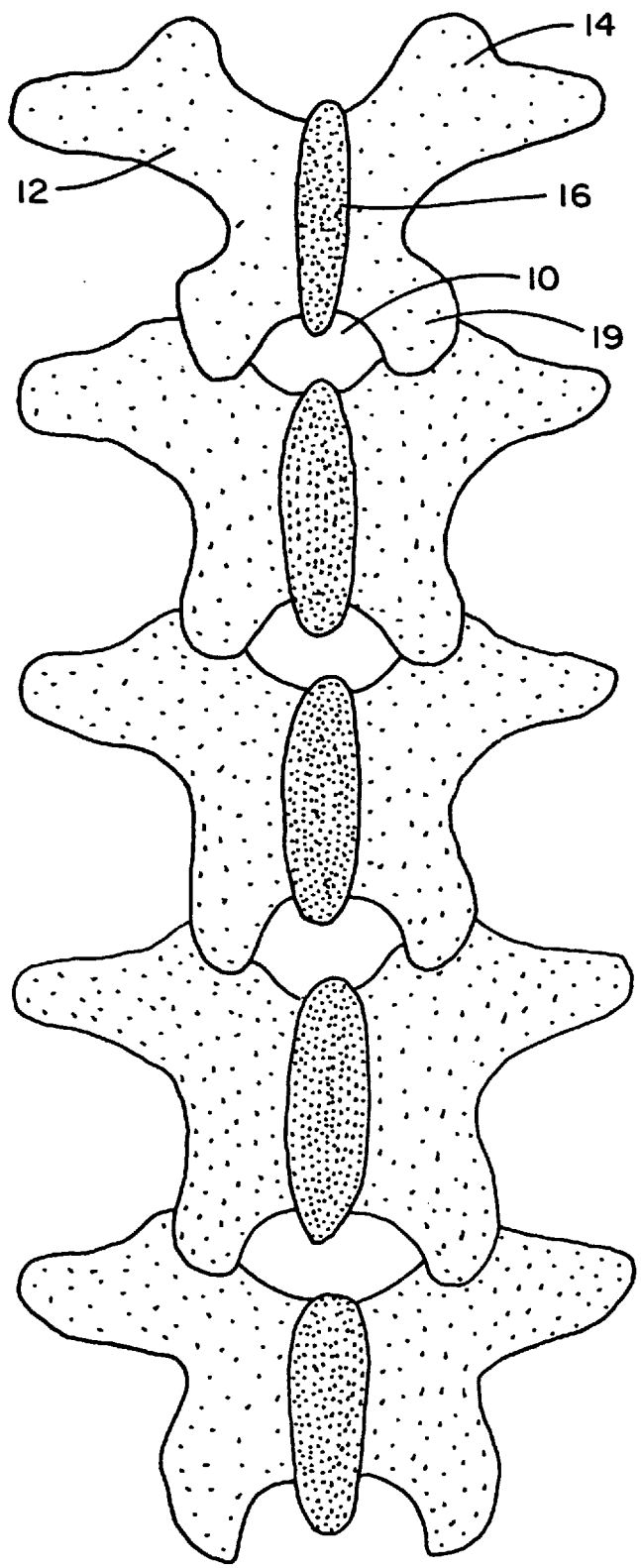
FIG. 3 is a posterior view of a sequence of vertebrae.
Figure 4:
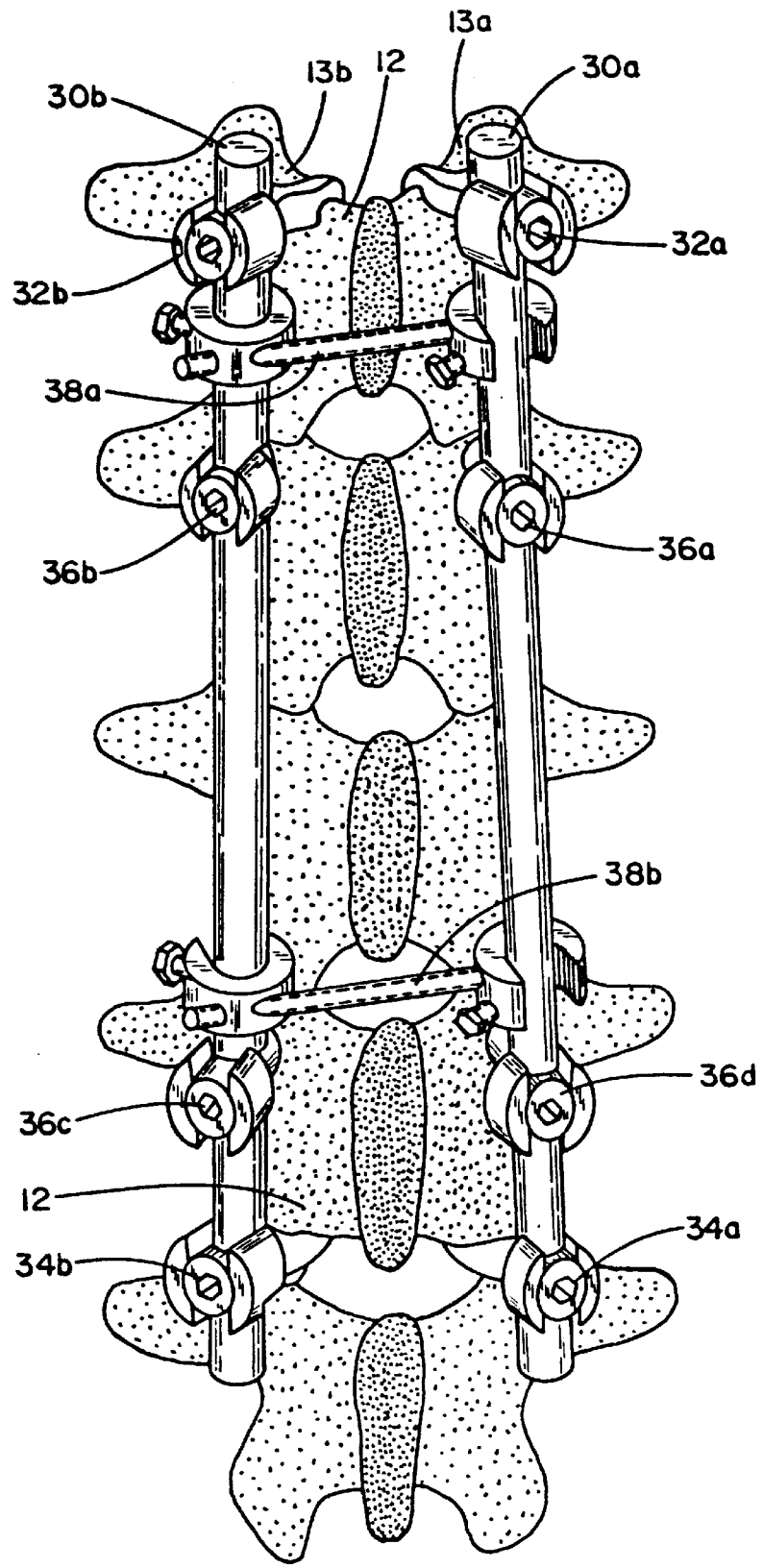
FIG. 4 is a posterior view of a hook, screw and rod system of the prior art.
Figure 5:
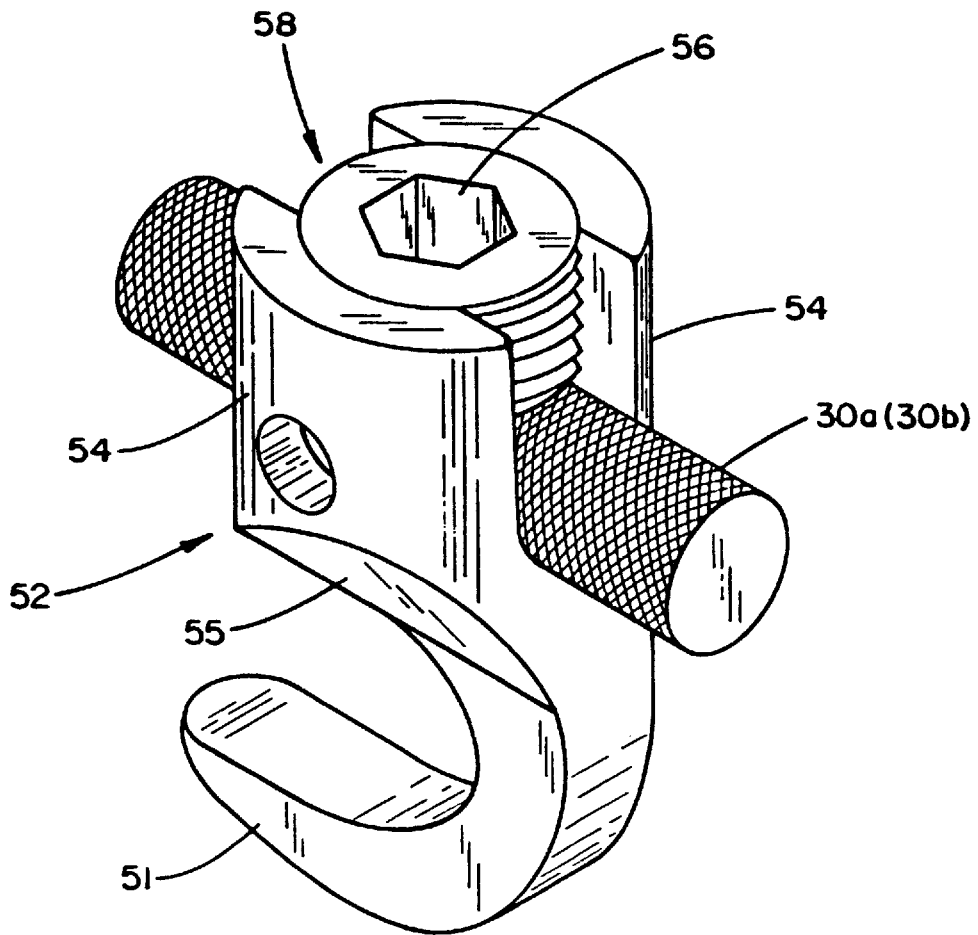
FIG. 5 is a side cross-sectional view of the hook device of the prior art apparatus of FIG. 4.
Figure 6:
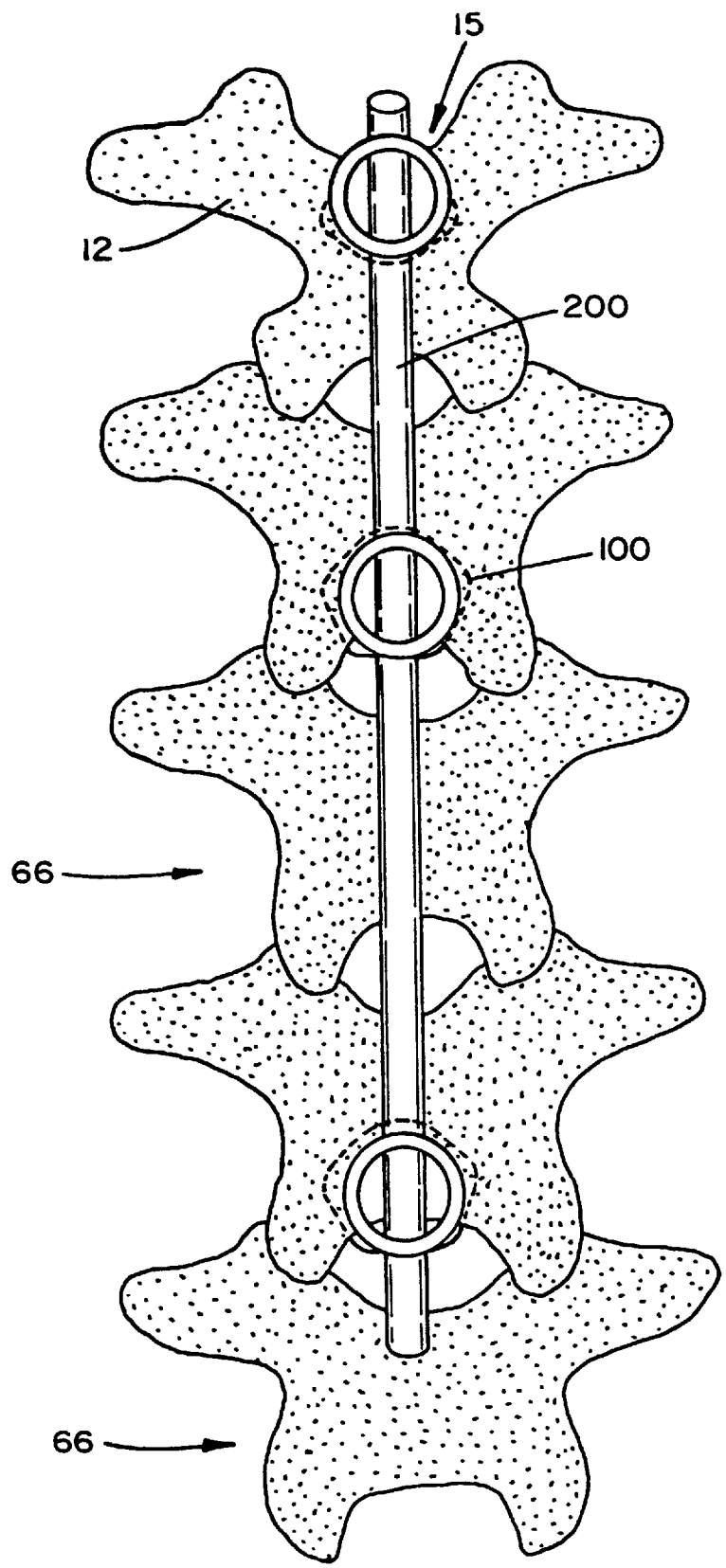
FIG. 6 is a posterior view of the hook and central rod apparatus of the present invention.

Referring now to FIG. 6, a posterior view of the centerline unitary rod and hook apparatus of the present invention is provided. As in FIG. 4, which illustrated a dual rod apparatus of the prior art, the present invention may be generally categorized as one which utilizes hooks to provide coupling of a rod to the spine, and which does so by being anchored under the lamina. More specifically, with respect to the present invention however, the hooks 100 are designed to be inserted under the arch 15 of the lamina 12, wherein the undersurface of the bone forms a shallow arch, or inverted-V shape. Inasmuch as the rod 200 of this embodiment of the present invention is intended to extend downward along the centerline of the spine, it may be necessary to remove the spinous processes of the sequence of vertebrae along which the rod 200 is to extend. This includes vertebrae 66 to which the hooks 100 are not mounted, but which are disposed between vertebrae which are coupled by the apparatus, or which are adjacent to the sequence which is to be instrumented, and may therefore be effected by the presence of the rod.

Figure 7:
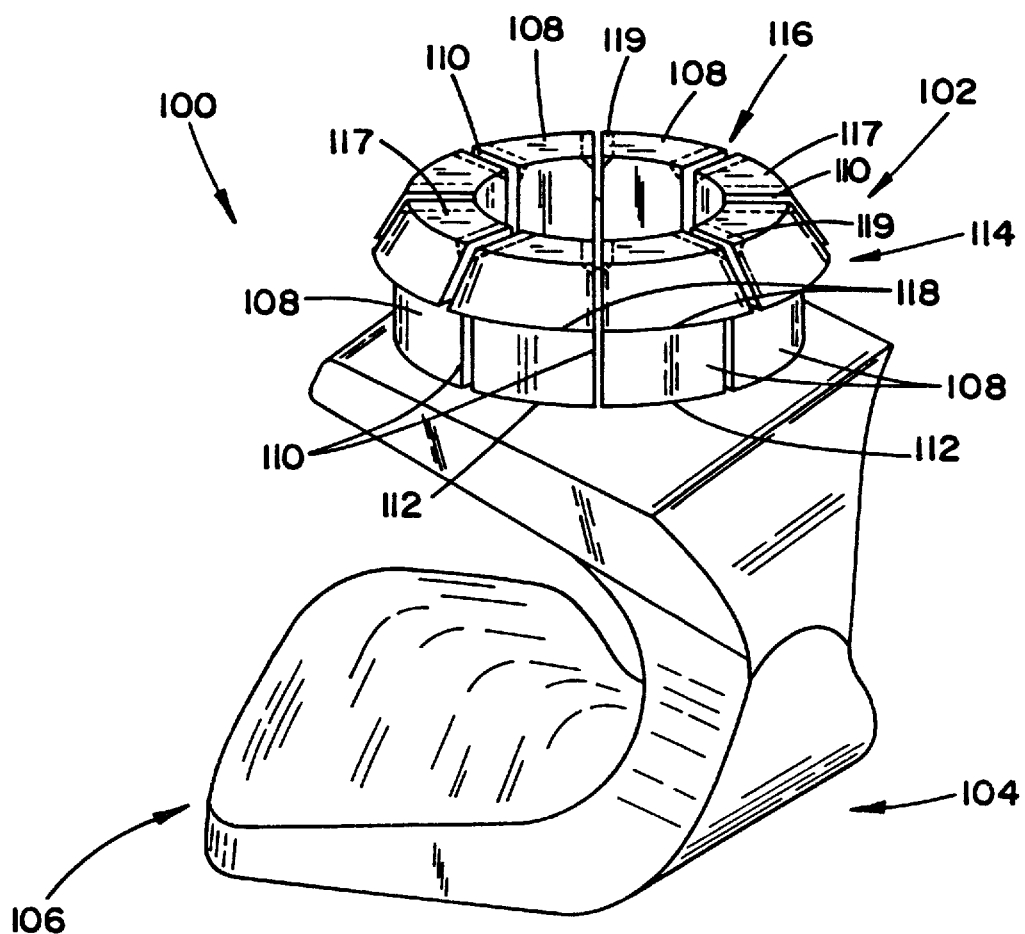
FIG. 7 is a side perspective view of a hook of the present invention.

Referring now to FIG. 7, the hook portion 100 includes a cylindrical top portion 102, an intermediate curvate lamina-cupping section 104, and an arched extending section 106 which is positionable beneath the lamina. The cylindrical top section 102 is comprised of a plurality of upwardly extending members 108 which mutually define the cylinder 102 and are separated by vertically oriented slots 110.

Each of the upwardly extending members 108 has a generally uniform radial thickness, thereby mutually defining a constant diameter for the cylinder 102, from its union 112 with the curvate lamina-cupping section 104, up to a circumferential position 114 near to the uppermost extent 116 thereof. The uppermost extent 116 thereof, however, comprises a discontinuously widening which subsequently tapers radially inwardly from that vertical position to the upper end of the members 108. This discontinuously widening thereby defines an annular ledge 118 around the cylindrical top section 102 which ledge 118 tapers inwardly to provide a beveled conformation.

In preferred embodiments (the features of which are illustrated hereby in phantom), the top surfaces 117 of the upwardly extending members 108 of the blade portion 100, which mutually define the cylindrical section 102, and which are rotationally freely retained in the interior axial bore of the head portion (set forth in alternative embodiments below with respect to FIGS. 8a and 8b), include ridges and/or curvate notches 119 which are diametrically paired across the cylindrical section 102. These notches 119 are so formed such that when a rod is seated thereon and provides a downward force, a resultant radial force, which is directed outward, is generated. It shall be understood that these notches 119 are positioned between adjacent pairs of the upwardly extending members 108 such that the vertical slots 110 separating each are widened by downward force of the rod thereon.

Figure 8A:
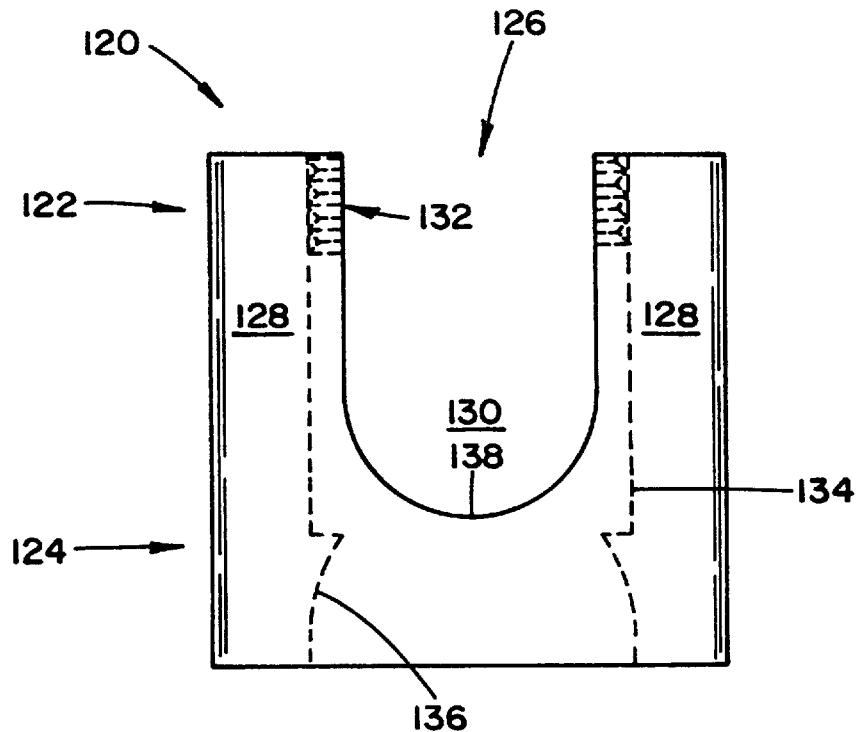
FIGS. 8a and 8b are side views of two alternative head portions of the present invention.
Figure 8B:
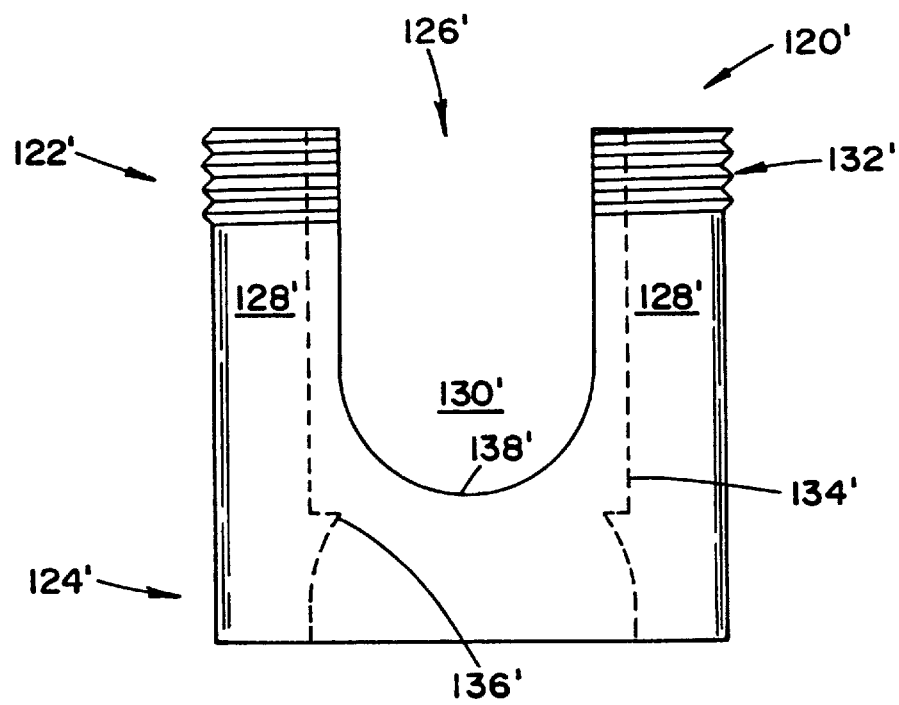

Referring now to FIGS. 8a and 8b, in which two alternative embodiments of the head portions of the present invention are provided in side views, each head portion 120,120' comprises a cylindrical shape having an upper section 122,122', a lower section 124,124', and an axial bore 126,126'. The upper section 120,120' of each embodiment is divided into a pair upwardly extending elements 128,128' which define therebetween a vertical channel 130,130' for receiving a rod (see FIG. 10). The upwardly extending elements 128,128' each comprise a threading 132,132' on a surface thereof for engaging a threaded top locking device (see FIGS. 9a and 9b). More specifically, in the embodiment shown in FIG. 8a includes a threading 132 on the inner surface of the upwardly extending elements 128, and the elements 128' of the embodiment shown in FIG. 8b includes a threading 132' on their outer surfaces. In either case, the threading 132,132' permits the engagement of a locking means which may be translated downwardly to provide a corresponding downward force onto the rod to secure the rod in the channel 130,130'.

The lower sections of each head portion 124,124' are identical, including an interior conformation on the inner surface 134,134' of the axial bore 126,126' which provides an interference locking means for securely holding the cylindrical top section 102 of the corresponding blade portion 100 therein. More specifically, the bore 126,126' of the head portion 120,120' comprises an inner annular lip 136,136' which engages the outer annular ledge 118 of the corresponding cylindrical top section 102 of the blade portion 100. Upon coupling, the tapered uppermost ends 116 of the upwardly extending individual members 108 of the blade portion 100 deflect inwardly until the annular ledge 118 advances beyond the inner annular lip 136,136' and they snap back to their undeflected position. The head 120,120' and blade portions 100 are thereby prevented from separating based on the interference fit of the ledge 118 and lip 136,136'.

The diameter of the annular lip 136,136' of the bore is substantially equivalent to the undeflected diameter of the cylindrical top section 102 such that once the blade 100 and head portion 120,120' are coupled, the two portions may rotate relative to one another. The relative position of the annular lip 136,136' within the axial bore 126,126' is set such that the uppermost end 116 of the cylindrical top section 102 of the blade portion 100 extend above beyond the deepest point of the curvate bottom 138,138' of the channel 130,130'. This requires that the rod, once inserted into the channel, rest on top of the cylindrical section 102 of the blade portion 100 (and not on the curvate bottom 138,138' of the channel 130,130').

Subsequent locking down of the rod in the channel 130,130', by a locking nut (see FIGS. 9a and 9b, which engage the threading 132,132' at the top 122,122' of the head 120,120') causes the head 120,120' to be drawn upwardly relative to the blade 100, until the interference of the annular lip 136,136' of the head 120,120' and the annular ledge 118 of the top cylinder 102 of the blade portion 100 engage. The friction of this interference serves to lock the head portion 120,120' at the rotational position, thereby preventing continued swiveling.

Figure 9A:
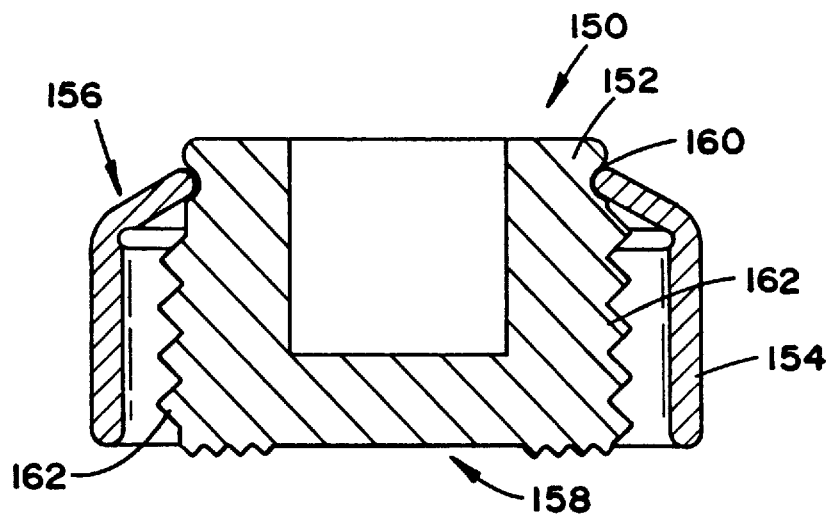
FIGS. 9a and 9b are side cross-section views of alternative top locking nuts which correspond to the head portions illustrated in FIGS. 8a and 8b respectively.
Figure 9B:
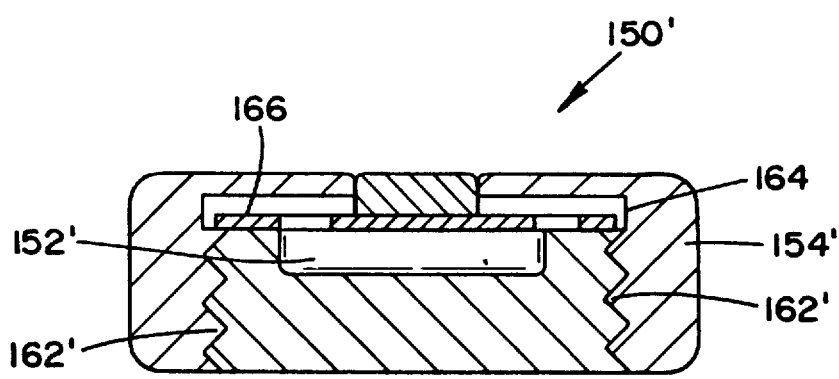

Referring now to FIGS. 9a and 9b, two corresponding unitary locking cap nuts 150,150', which are designed to mate with the threading 132,132' at the top of the head portions 120,120', is set forth hereinbelow. It shall be understood, however, that these unitary locking cap nuts are not the only nuts which may be utilized for the purpose of locking the rod in the channel 130,130'. Further, these unitary locking cap nuts are more fully set forth in co-pending application U.S.S.N. 08/641,504, entitled "A Unitary Locking Cap For Use With A Pedicle Screw", assigned to the assignee of the present invention, the disclosure of which is incorporated herein by reference.

More specifically with respect to FIG. 9a, which is utilized with the head portion 120 shown in FIG. 8a, the unitary locking cap 150 has a rotationally freely coupled central post 152 and an outer rim 154, the two elements being concentric. The rim 154 has a concentric hole in the otherwise closed top end 156, and an open bottom end 158. The diameter of the top hole is approximately equal to the width of the post portion 152. The post portion 152 in this embodiment has a generally cylindrical shape having small annular recess 160 formed near the top end thereof so that is nests in the top hole of the cylindrical rim 154. The post 152 includes a threading 162 which engages the threading 132 of the head portion 120 and locks the rod in the channel 130.

In the embodiment shown in FIG. 9b, the interior surface of the cylindrical rim 154' portion has a threading 162' which corresponds to the threading 132' on the outer surfaces of the head portion 120'. Correspondingly, the central post 152' is smooth, and is concentrically and coaxially mounted in the rim 154'. The mutual means by which rotational freedom, but secure retention of the post 152' within the rim portion 154' are an annular recess 164 in the inner wall of the rim 154' and a plurality of outwardly extending spring deflecting arm elements 166 which seat in the annular recess 164 to permit the post 152' to rotate, yet be retained and not removed.

Figure 10:
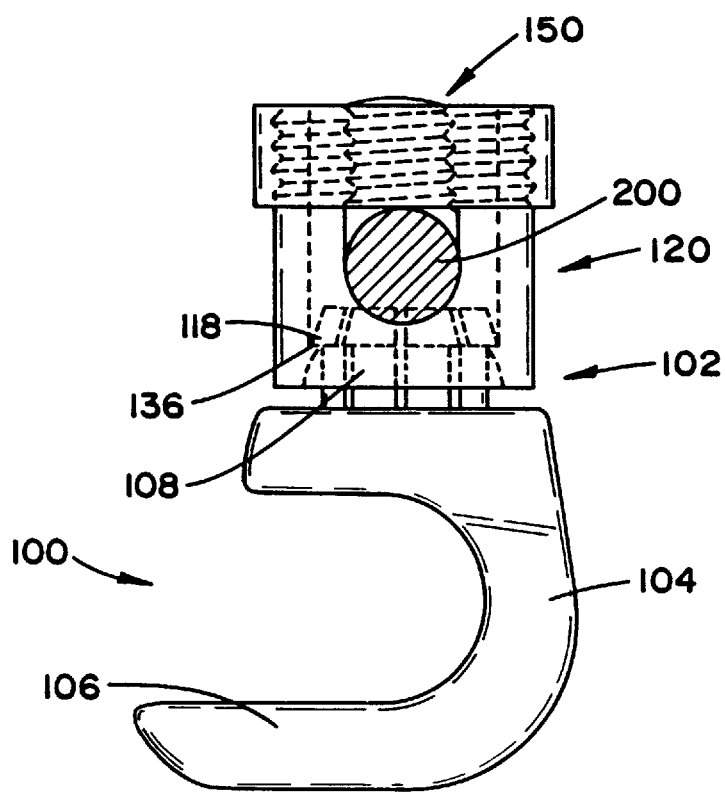
FIG. 10 is a side view of a fully assembled hook of the embodiment of the present invention.

Referring now to FIG. 10, in which a fully assembled hook and rod assembly of the type described hereinabove is shown, the assembly process of this device is set forth. Prior to the surgeon encountering the device, the head portion 120 is advanced downwardly onto the upper cylindrical section 102 of the blade portion such that the constituent upwardly extending members 108 are deflected inward until the ledges 118 thereof, and the lip 136 of the head portion 120 engage to form an interference fit. During implantation of this invention, the flat extending section 106 of the blade portion 100 is first positioned under the corresponding lamina. The head element 120 is then rotated relative to the blade 100, such that the rod 170 may be easily inserted into the channel formed therein. The rod 170 is positioned in the channel such that it rests on the top of the cylindrical top section 102 of the blade portion 100. The locking nut 150 causes the rod 170 to push down on the cylinder 102, and to secure the head 120 from rotating relative to the blade 100 via the friction lock of the interfering lip 118 and ledge 136.

While there has been described and illustrated a set of embodiments of a lamina hook which may be placed at the central axis of the spine, beneath the arched portion of the lamina, having mutually rotating head and blade portions, it will be apparent to those skilled in the art that variations and modifications are possible without deviating from the broad spirit and principle of the present invention. The present invention shall, therefore, be limited solely by the scope of the claims appended hereto.

We claim:

1. A rotational hook device for use with orthopedic rod implantation apparatus, comprising:

a head portion including a rod receiving channel and an axial bore, said axial bore having an inwardly directed annular lip;

an arched blade portion, positionable against an arched undersurface of a lamina along the central posterior axis of a sequence of spinal bones, having a top section which is extendable above the lamina including a plurality of upwardly extending members which form an axially segmented cylindrical section, said upwardly extending members each having a thickened portion thereof which thickened portions collectively define a circumferential annular ledge around the outer axial extent of the cylindrical section, said cylindrical section being insertable into said axial bore of said head portion such that the annular ledge of the blade portion is advanced beyond the annular lip of the head portion, a top surface of said cylindrical section extends above a bottom of said rod receiving channel, and such that said head and blade portions are initially rotationally independent; and means for securing a rod in said rod receiving channel;

whereby insertion of the rod in the rod receiving channel, and application of the means for securing said rod in said channel, causes said annular ledge to contact and interference fit against the annular lip in the axial bore of the head portion thereby preventing rotational movement the blade and head portions.

2. The rotational hook device of claim 1, wherein said head portion further includes a threading on an upper section thereof, and wherein said means for securing a rod in said rod receiving channel comprises a nut.

3. The rotational hook device of claim 1, wherein said rod receiving channel is vertically aligned and defined between two upwardly extending members.

4. The rotational hook device of claim 1, wherein said rod receiving channel is horizontally aligned and formed in the side of said head portion.

5. An orthopedic rod implantation apparatus, comprising:

at least one elongate rod;

a plurality of polyaxial hook assemblies for coupling said elongate rod to lamina of a spine, each of said hook assemblies including;

a head portion including a rod receiving channel and an axial bore, said axial bore having an inwardly directed annular lip;

a arched blade portion, positionable against an undersurface of a lamina along a central posterior axis of a sequence of spinal bones, having a top section which is extendable above the lamina including a plurality of upwardly extending members which form an axially segmented cylindrical section, said upwardly extending members each having a thickened portion thereof which thickened portions collectively define a circumferential annular ledge around the outer axial extent of the cylindrical section, said cylindrical section being insertable into said axial bore of said head portion such that the annular ledge of the blade portion is advanced beyond the annular lip of the head portion, a top surface of said cylindrical section extends above a bottom of said rod receiving channel, and such that said head and blade portions are initially rotationally independent; and means for securing a rod in said rod receiving channel;

whereby insertion of the rod in the rod receiving channel, and application of the means for securing said rod in said channel, causes said annular ledge to contact and interference fit against the annular lip in the axial bore of the head portion thereby preventing rotational movement the blade and head portions.

6. The rotational hook device of claim 5, wherein said head portion further includes a threading on an upper section thereof, and wherein said means for securing a rod in said rod receiving channel comprises a nut.

7. The rotational hook device of claim 5, wherein said rod receiving channel is vertically aligned and defined between two upwardly extending members.

8. The rotational hook device of claim 5, wherein said rod receiving channel is horizontally aligned and formed in the side of said head portion.

* * * * *